United States Patent [19]

Aegidius et al.

[11] 4,239,394
[45] Dec. 16, 1980

[54] LIQUID ANALYZING APPARATUS

[75] Inventors: Poul E. Aegidius, Helsinge; Miloslav Zakora, Hillerød; Jorgen F. Nielsen, Allerød, all of Denmark

[73] Assignee: A/S Foss Electric, Hillerod, Denmark

[21] Appl. No.: 894,389

[22] Filed: Apr. 7, 1978

[30] Foreign Application Priority Data

Apr. 8, 1977 [SU] U.S.S.R. ............................. 2480802

[51] Int. Cl.³ .......................................... G01N 21/01
[52] U.S. Cl. .................................... 356/436; 250/573
[58] Field of Search .................... 356/409–419, 356/426, 436, 440, 445, 36, 442; 23/231; 277/DIG. 6, 228, 165; 222/386, 401; 417/545; 250/573

[56] References Cited

U.S. PATENT DOCUMENTS

| 2,578,523 | 12/1951 | Llewellyn | 277/DIG. 6 |
|---|---|---|---|
| 2,752,815 | 7/1956 | Batchelor | 356/36 |
| 2,792,790 | 5/1957 | Capps | 92/249 |
| 2,844,067 | 7/1958 | Borg | 356/414 X |
| 2,844,421 | 7/1958 | Hayman | 277/DIG. 6 |
| 3,442,623 | 5/1969 | Aegidius | 23/231 |
| 3,800,984 | 4/1974 | Phelan | 222/137 |
| 3,871,782 | 3/1975 | Johansson et al. | 403/122 |
| 3,877,817 | 4/1975 | Ralston | 356/414 X |
| 3,972,625 | 8/1976 | Takahasi et al. | 356/435 |

FOREIGN PATENT DOCUMENTS 233634 2/1960 Australia.
242746 2/1960 Australia.
263795 12/1965 Australia.

Primary Examiner—John K. Corbin
Assistant Examiner—Bruce Y. Arnold
Attorney, Agent, or Firm—Dennison, Meserole, Pollack & Scheiner

[57] ABSTRACT

The invention relates to a liquid analyzing apparatus, especially for use in determining the fat content of milk samples. The apparatus comprises manually operated dosage syringes or pumps for mixing diluent and liquid sample in a predetermined relationship, a manually operable homogenizer for providing homogenized mixture to photometric measuring means including a cuvette. The homogenizer and the photometric measuring means are arranged within a temperature controlled block or body made from a heat conductive material. The homogenizer may comprise a piston pump having a piston provided with an O-ring and rigidly connected to a piston rod oscillating angularly in operation.

17 Claims, 3 Drawing Figures

LIQUID ANALYZING APPARATUS

BACKGROUND OF THE INVENTION

The present invention relates to a liquid analyzing apparatus in general and especially (but not exclusively) to an apparatus of the type used for determining the fat content of milk or related liquids.

In such liquid analyzing apparatuses it is general practice to mix the milk sample with some kind of diluent before the sample is passed through a homogenizer adapted to break at least some of the larger fat globules of the milk down into smaller fat globules.

SUMMARY OF THE INVENTION

The present invention has for its object to provide an improved apparatus for analyzing fat content of milk or related liquids. The improved apparatus according to the invention is reliable in use, manufacture, and maintainance, and furthermore, it is relatively simple and inexpensive and may be used to analyze relatively small samples of liquid or milk. Additionally, the electrical power consumption of the apparatus is relatively small.

The present invention provides a liquid analyzing apparatus, especially for determining the fat content of milk samples, and comprising means for mixing a liquid sample with diluent, means for homogenizing the mixture of liquid sample and diluent, photometric measuring means adapted to measure a constituent of the sample in the mixture, means for passing the homogenized mixture to said photometric measuring means, a block or body made from a heat conductive material, and means for thermostatically controlling the temperature of said block or body, said homogenizing means and said photometric measuring means being arranged within said block or body. This structure provides a very simple thermostatic temperature control of the homogenized sample on which measurement is being made. The apparatus may further comprise a diluent reservoir which is connected to the mixing means by a passage or tube surrounding the block and being in heat conductive contact therewith. Thereby the diluent may be heated to a suitable, predetermined temperature before it is mixed up with the liquid sample or milk sample to be analyzed.

The homogenizing means may comprise a piston pump including a cylinder, a piston rigidly connected to one end of a piston rod and having a circumferentially arranged O-ring sealingly engaging with the inner wall of the cylinder, and driving means which are connected to the other end of the piston rod by means of a joint of the type allowing movement in all directions, and which are adapted to reciprocate the piston and piston rod axially while angularly oscillating them in relation to the longitudinal axis of the cylinder. It has surprisingly been found that the O-ring may provide the necessary tightness between the reciprocating and oscillating piston and the inner cylinder wall. The use of the O-ring makes it possible to manufacture the cylinder and piston with relatively big tolerances, and the dead space of the pump may be made relatively small which reduces the necessary amount of a liquid sample to be analyzed. The O-ring is preferably backed up by a ring of Teflon or another plastic material.

The homogenizing effect of a homogenizer formed as a piston pump is normally obtained in a number of ball valves arranged in the outlet of the pump. In the apparatus according to the invention the piston pump may also have an outlet with a ball valve including a ball biased towards its valve seat by a spring member, and a piston which is displaceably and sealingly arranged in a cylindrical bore may then be interposed between and engage the ball and the biasing spring member. This structure considerably reduces the dead space of the ball valve, whereby the total dead space of the homogenizer is further reduced. Due to the fact that the small dead space renders it possible to use relatively small samples of the liquid to be analyzed the wearing effect to which the ball valve is exposed is diminished to such an extent that the use of a single ball valve is sufficient.

In principle, the apparatus according to the invention may be of the automatic or semi-automatic type. In order to reduce consumption of electrical power the homogenizer may, however, be adapted to be operated manually.

BRIEF DESCRIPTION OF THE DRAWING

The invention will now be further described with reference to the drawings illustrating diagrammatically an embodiment of the apparatus according to the invention which should be interpreted as an example rather than in a limiting sense.

In the drawings

DESCRIPTION OF THE PREFERRED EMBODIMENT

Figure 1:
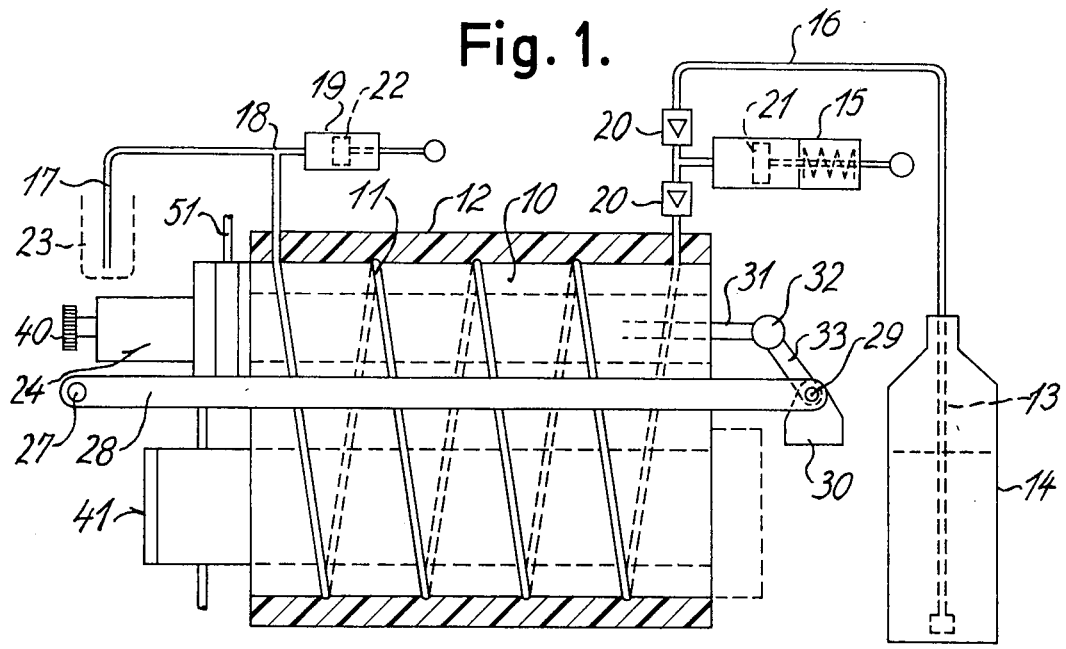
FIG. 1 illustrates diagrammatically a side view and partially sectional view of an embodiment of the apparatus according to the invention.
Figure 2:
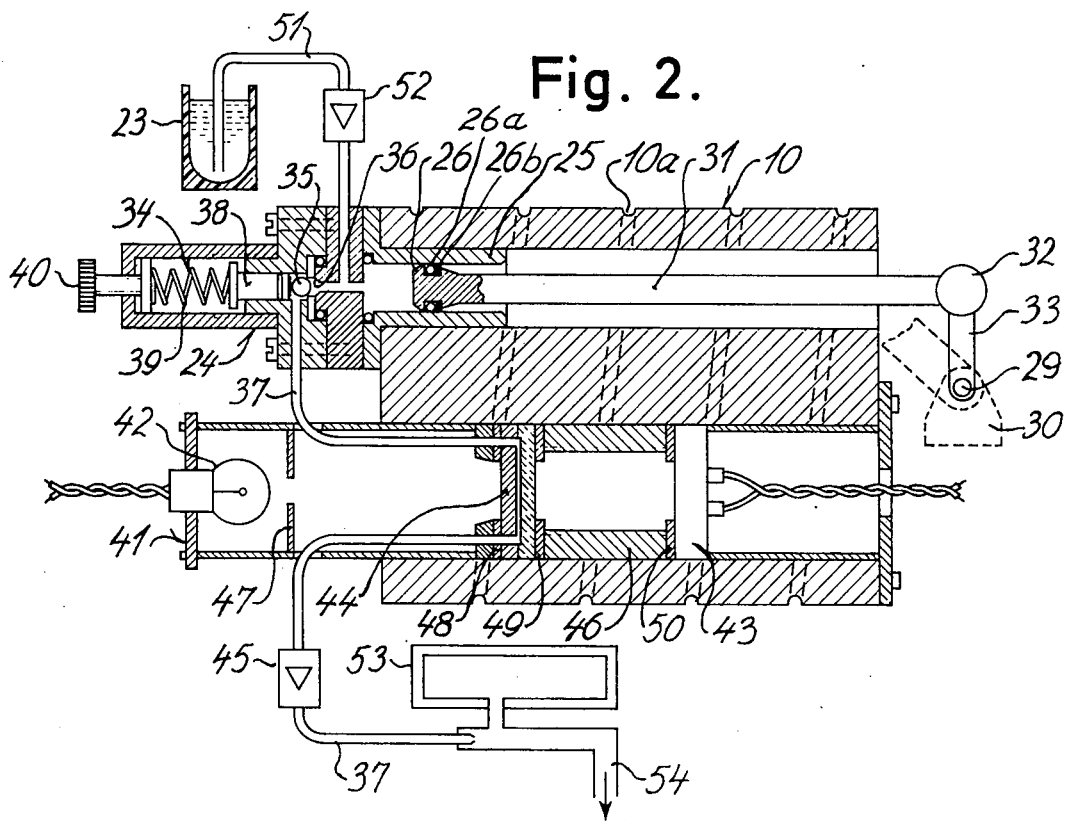
FIG. 2 shows a further diagrammatic sectional illustration of the apparatus shown in FIG. 1, some parts having been omitted and other having been illustrated more in detail.

The apparatus shown in the drawings comprises a cylindrical block or body 10 of a heat conductive material, such as metal, preferably aluminum or an aluminum alloy. In the outer cylindrical surface of the block 10 a helical groove 10a receiving a tube or conduit 11, for example of stainless steel, is formed. The cylindrical surface of the block 10 and the helically extending tube 11 is surrounded by a layer 12 of a heat insulating material. One end of the tube or conduit 11 is connected to a dip tube 13 in a storage container or reservoir 14 for diluent. A diluent dispensing syringe or dosage pump 15 is connected to a section 16 of the tube 11 extending between the block 10 and the dip tube 13. The opposite end of the tube 11 is connected to a sample aspirating tube or cannula 17 at a branching off point 18, at which point a sample aspirating syringe or dosage pump 19 is also conncted to the aspirating tube 17. The components described constitute a system for dispensing and mixing metered amounts of liquid sample and diluent, and this system may be operated as follows:

The tube section 17 is provided with a one-way valve 20 at either side of the position at which the diluent dispensing syringe is connected so that by operating a spring biased piston 21 of the syringe 15 the tube section 16, the tube 11, and the sample aspirating tube 17 may be completely filled with the diluent. As will be described more in detail below, the temperature of the block 10 is controlled by a temperature controlling device so that the diluent contained in the tube 11 is heated to and maintained at a substantially constant, predetermined temperature. When a liquid sample, for example a milk sample, is to be mixed with diluent, a piston 22 in the sample aspirating syringe 19 is displaced from its retracted or backward position to its advanced or forward position whereby a volume of diluent corresponding to the stroke volume of the syringe 19 is discharged from the tube or cannula 17. The tube or cannula 17 is now dipped into the liquid sample, and the piston 22 is displaced to its retracted position whereby a metered volume of liquid sample corresponding to the stroke volume of the syringe 19 is aspirated into the tube or cannula 17. Preferably, the said stroke volume of the syringe 19 is equal to or less than the volume of the tube bore extending from the free end of the tube 17 to the branching off point 18, so that the liquid sample aspirated into the tube 17 does not pass beyond the point 18. The piston 21 of the diluent dispensing syringe 15 is spring biased towards its retracted or backward position and is maintained in that position when the piston is not operated. A mixing container or cup 23 is now arranged below the free end of the aspirating tube or cannula 17, and thereafter the piston 21 of the diluent dispensing syringe 15 is manually moved from its retracted to its advanced or forward position. The stroke volume of the diluent dispensing syringe 15 substantially exceeds the stroke volume of the sample aspirating syringe 19, and therefore the described displacement of the piston 21 involves discharge of the metered liquid sample contained in the tube or cannula 17 and of an amount of diluent corresponding to the difference in stroke volume of the diluent dispensing syringe 15 and of the diluent aspirating syringe 19, into the mixing container or cup 23. The cup 23 preferably has a hemispherical inner bottom surface as shown in FIG. 2, and if the cannula 17 is arranged excentrically in the cup an automatic mixing of milk sample and diluent may be obtained when the latter is expelled into the cup 23.

The temperature control means for controlling the temperature of the block 10 may comprise a temperature sensing device, for example a thermistor (not shown) arranged within the block, and an electrical heating device, for example a power transistor (not shown) arranged on one of the end surfaces of the block, and in order to prevent unnecessary loss of heat so as to keep the power consumption of the apparatus at a minimum the whole apparatus may be surrounded by a heat insulating housing (not shown). This is of special importance in case the apparatus is battery operated.

The apparatus also includes a homogenizer 24 for homogenizing the mixture of the liquid sample or milk sample and diluent. This homogenizer comprises a cylinder 25 mounted in the block 10 and containing a piston 26 (FIG. 2) which may be reciprocated axially within the cylinder 25 by oscillating a manually operable handle 27 which is mounted on a lever or rod 28 fixedly mounted at one end of a shaft 29 which is journaled in bearings 30 mounted on a base plate (not shown). The piston 26 is formed as an integral part of a piston rod 31 which by means of a ball joint 32 or the like is connected to an arm 33 fixedly mounted on the shaft 29.

The piston 26 has a circumferentially extending annular groove receiving an O-ring 26a or a similar sealing member tightly engaging the inner surface of the cylinder 25, and the O-ring is supported by an annular disc of backing ring 26b of plastic material such as Teflon. When the homogenizer is operated by moving the handle 27 up and down the arm 33 is swung to and fro whereby the piston 26 and the piston rod 31 are reciprocated axially in the cylinder 25. During reciprocation the angular position of the piston and piston rod in relation to the longitudinal axis of the cylinder 25 will change, and therefore, the piston 26 has tapered circumferential surface parts at either side of the groove receiving the O-ring 26a and the backing ring 26b in order to prevent that other parts of the piston than the O-ring and the backing ring come into direct contact with the cylinder 25.

The homogenizer comprises a ball valve 34 including a ball 35 and a valve seat 36 positioned in an outlet conduit or passage 37 which communicates with the cylinder 25. The ball 35 is in contact with one end surface of a piston member 38 which is displaceably mounted in a bore and sealingly engages the inner wall thereof. The piston member is biased towards the ball by a spring 39 engaging the other end surface of the piston member 38, and compression of the spring may be adjusted by means of an adjustment screw 40.

The apparatus also comprises a photometric measuring device 41 comprising a light source 42 irradiating a photoelectric cell 43 through a measuring cuvette 44 forming part of the outlet conduit 37. Downstream of the cuvette 44 a one-way valve 45 is inserted in the outlet conduit 37. The valve 45 is adapted to maintain a pressure within the cuvette and the outlet conduit slightly exceeding that of the atmosphere in order to reduce the risk that gas bubles are formed in the conduit or cuvette. The photometric measuring device 41 further comprises a spacing tube 46 positioned between the photoelectric cell 43 and the cuvette 44, and a number of axially spaced diaphragm members 47-50. It is important that the inner surfaces of the space defined between the photoelectric cell and the cuvette is highly light absorbing. Therefore, the inner surface of the spacing tube 46 is preferably made rough, for example by forming a fine internal thread therein. Electrical current is supplied to the light source 42 through a voltage stabilizing circuit (not shown), and the photoelectric cell 43 is electrically connected to a suitable electronic circuitry which may include an analog measuring circuit adapted to convert the current signals received from the photoelectric cell 43 into analog signals representing the constitutent of the liquid sample measured, for example the fat content of a diluted milk sample. The output signals of the analog circuit may be transmitted to a digital measuring circuit converting the analog signals into digital units which may then be displayed by a suitable displaying device. Electrical power may be supplied to the temperature control means, the light source 42, and the measuring circuits from any suitable power source (not shown), for example a battery or from an electric supply network. The electronic circuitry mentioned above is preferably heat insulated from the block 10 so as to not interfere with the temperature control of the block 10.

The homogenizer cylinder 25 also communicates with an inlet passage or conduit 51 containing a one-way valve 52. When a mixture of a metered liquid sample and a metered amount of diluent has been prepared as previously described, the cup or container 23 containing the mixture is placed below the homogenizer conduit 51 so that the free end thereof dips into the mixture (FIG. 2). Then the handle 27 is moved up and down a few times. The corresponding reciprocating movement of the piston 26 causes the mixture from the cup 23 to be alternately aspirated into the cylinder 25 and expelled therefrom under a rather high pressure through the ball valve 34, the outlet conduit 37, and the cuvette 44. When the mixture of milk and diluent passes through the valve 34 and is exposed to a sudden pressure relief at least some of the fat globules in the milk are broken down into smaller fat globules. Due to the fact that the dead space of the homogenizer pump as well as the inner space of the ball valve 34 which forms part of the outlet conduit 37 are relatively small it is sufficient to pass a relatively small amount of each sample through the homogenizer, the outlet conduit 37, and the cuvette 44 in order to ensure that the preceding sample is effectively flushed out before a new measurement is made as described below. It is, of course, in itself advantageous that relatively small amounts of milk sample and diluent are necessary in the apparatus according to the invention. However, the use of small samples also has the effect that the inevitable wear of the ball 35 of the ball valve 34 is considerably reduced which involves that a single ball valve is sufficient, whereas a plurality of valves has to be used in known apparatuses of the type in question.

When the cuvette 44 has been filled with the homogenized sample or mixture it is possible to measure one or more constituents of the milk sample, for example the fat content, by means of the photometric measuring device 41 in a well-known manner. The result of the measurement may be directly displayed as explained above.

The apparatus shown may comprise a drip pan or spillage collecting tray diagrammatically indicated at 53 in FIG. 2. The pan or tray 53 serves to collect spillage, for example liquid dripping from the cannula 17 due to expansion of diluent when heated in the conduit 11 surrounding the block 10. The pan or tray has an outlet tube 54, and in order to promote discharge of spillage liquid from the tray the outlet conduit of the homogenizer opens into the outlet tube 54 as indicated in FIG. 2, whereby a suction effect is created by the liquid which is discharged through the conduit 37 when the homogenizer 24 is operated by an operator moving the handle 27 as described above.

Figure 3:
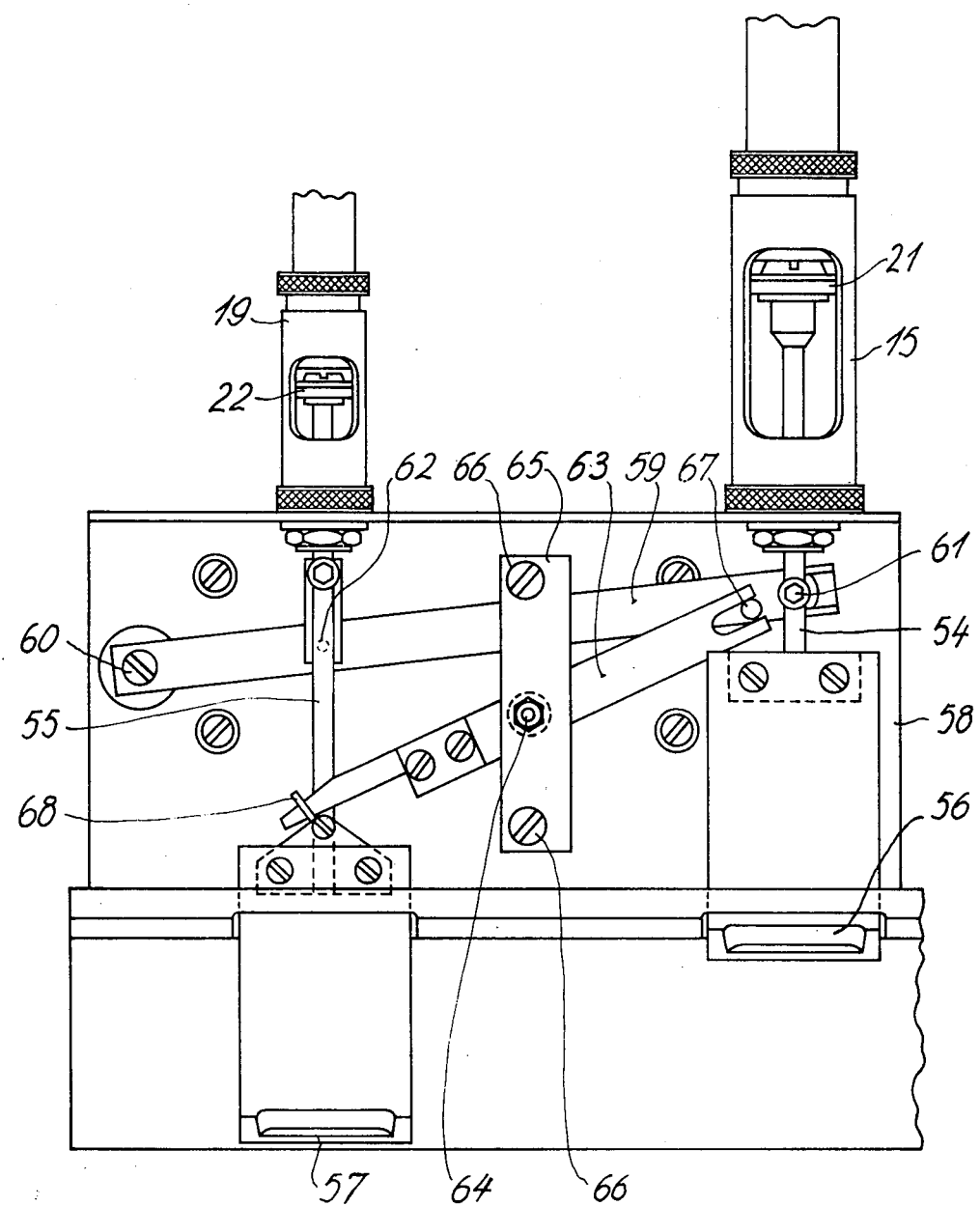
FIG. 3 is a plan view of part of a modified embodiment in an enlarged scale.

In order to obtain accuracy of a measurement it is important that the sample and the diluent are mixed in an accurate predetermined ratio which is determined by the respective stroke volumes of the syringes or pumps 15 and 19. If, however, the operator of the apparatus does not make sure that the pistons 21 and 22 are pressed right to their top dead centers when operated the desired predetermined ratio is not obtained. FIG. 3 shows an embodiment in which the pistons 21 and 22 of the syringes or pumps 15 and 19 are interconnected by a lever system by means of which the pistons 21 and 22 may be operated simultaneously. The lever system also secures the desired proportion or ratio of the mixture even when the pistons 21 and 22 are not moved all the way to their bottom dead centers under their suction strokes. In FIG. 3 the pistons 21 and 22 are mounted at one end portion of piston rods 54 and 55, respectively, and push buttons 56 and 57 which are slideably mounted in relation to a frame part 58 of the apparatus, are connected to the other end of the piston rods as shown. The lever system interconnecting the piston rods comprises a lever 59, one end of which is swingably mounted at 60 to the frame part 58, the other end of the lever 59 being in pivotable engagement with the piston rod 54 at 61. Furthermore, the lever 59 is pivoted to the piston rod 55 at 62, whereby the piston rods 54 and 55 are forced to move together with the lever 59 along stroke lengths being related as the ratio of the distance between the pivots 60 and 61 to the distance between the pivots 60 and 62. A second lever 63 is mounted swingably at 64 on a bridge portion 65 fixed to the frame part 58 by means of screws 66. The bridge portion 65 extends transversely to and above the levers 59 and 63. A slot formed at one end of the lever 63 is in engagement with a stud 67 formed on the lever 59, and the other end of the lever 63 is in engagement with a hook member 68 connected to the push button 57 mounted slideably in relation to the frame part 58 and to the piston rod 55.

In FIG. 3 the button 56 is shown in its depressed position, and the pistons 21 and 22 are positioned at their top dead centers. When the operator depresses the push button 57 and thereby moves it inwardly in relation to the frame part 58 and the piston rod 55, the lever 63 is swung clockwise about the pivot 64. This movement of the lever 63 causes the lever 59 to swing clockwise about the pivot 60 whereby the piston rods 54 and 55 and 21 and 22 are moved from their top dead centers towards their bottom dead centers so as to aspirate liquid sample into the tube or cannula 17 and aspirate diluent from the storage container 14 into the syringe 15. When the push button 57 has been depressed the push button 56 is moved outwardly to its extended position together with the piston rod 54. The operator may now depress the push button 56 whereby the levers 59 and 63 are moved counterclockwise. This movement of the lever 59 causes movement of the pistons 21 and 22 from their bottom dead centers to their top dead centers whereby liquid sample and diluent is discharged from the cannula 17 as previously described.

EXAMPLE

In a specific embodiment of the apparatus described for measuring the fat content of milk samples, the block 10 is made from an aluminum alloy and has a diameter of 100 mm and a length of 110 mm. The temperature control means are adapted to maintain the temperature of the block 10 at a temperature of 60° C.±0.5° C. The block 10 is heated by a power transistor of the type TIP 145 (Darlington PNP). The transistor and an associated series resistance which supply the necessary heat to the block 10 is mounted on the end surface of the block.

The stroke volumes of the syringes 15 and 19 are 6.5 ml and 0.5 ml, respectively. The bore volume of the aspirating tube 17 from its free end to the branching off point 18 is 0.5 ml, and the bore volume of the helical part of the tube 11 surrounding the block 10 is approximately 13 ml. Thus, in a mixture of milk and diluent made by means of the apparatus the ratio of diluent plus milk and milk is 6.5:0.5=13. The diluent is of the type described by G. Haugaard and I. D. Pettinati, Journal of Dairy Science, August, 1959, Vol XLII, No. 8, 1255–1275.

The inner diameter of the homogenizer cylinder 25 is 12 mm, and the length of the stroke of the piston 26 is 18 mm. The lengths of the piston rod 31, the arm 33, and the lever 28 are 20 cm, 2 cm, and 40 cm, respectively, and during operation the piston rod 31 is tilted angularly 0.7° to either side of the longitudinal axis of the cylinder 25. If, for example a manual force of 5 kilogram is supplied to the handle 27 a homogenizing pressure of about 100 kg/cm$^2$ may be obtained within the homogenizer cylinder 25, and by moving the handle 27 so that the piston 21 is moved through three full strokes, a total liquid volume of about 6 ml will be aspirated into and expelled from the homogenizer.

It is surprising that the O-ring 26a is able to satisfactorily perform its sealing function under the heavy conditions to which it is exposed. Despite the high pressure provided within the cylinder 25 and the tilting angular movements of the piston 26 the O-ring 26a has a relatively long useful life. Experiments have shown that one and the same O-ring may be used for more than 150,000 samples (corresponding to more than 450,000 double strokes of the piston 26 if three double strokes are used for each sample), even if the pressure within the cylinder 25 amounts to about 80 kg/cm$^2$.

It should be understood that various modifications of the embodiments described above may be made without departing from the scope of the present invention.

We claim:

1. A liquid analyzing apparatus for determining the fat content of milk samples or the like, comprising means for mixing a liquid sample with diluent and means for homogenizing the mixture of the liquid sample and diluent and for passing the homogenized mixture to photometric measuring means adapted to measure a constituent of the sample in the mixture, the homogenizing means and the photometric measuring means being arranged within a body which is made from a heat conductive material and which has means for thermostatically controlling the temperature of said body, said mixing means comprising a dosage piston pump for the diluent and a dosage piston pump for the liquid sample, the pistons of said pumps being interconnected by a lever system so as to control movement thereof in accordance with a predetermined ratio or relationship.

2. A liquid analyzing apparatus especially for determining the fat content of milk samples, comprising:
   means for mixing a liquid sample with a diluent;
   photometric measuring means for measuring a given constituent of the sample in the mixture; and
   means associated with the mixing means for homogenizing the mixture of the liquid sample and diluent and for passing the homogenized mixture to the photometric measuring means, said homogenizing means comprising a piston pump having an outlet communicating with said photometric measuring means, said homogenizing means further comprising a ball valve including a ball biased toward a valve seat by a spring member, the piston pump further including a piston which is displaceable and sealingly arranged within a cylindrical bore interposed between and engaged by said valve ball and the biasing spring member.

3. A liquid analyzing apparatus according to claim 2, wherein said photometric measuring means comprises a cuvette communicating with said homogenizing means and having a discharge conduit, said discharge conduit including a valve adapted to secure a superatmospheric pressure within said cuvette.

4. A liquid analyzing apparatus according to claim 2, wherein said mixing means comprise a dosage piston pump for the diluent and a dosage piston pump for the liquid sample, the pistons of said dosage pumps being interconnected so as to control movement thereof in accordance with a predetermined ratio or relationship.

5. The liquid analyzing apparatus according to claim 2 and further comprising:
   a body member within which the homogenizing means and the photometric measuring means are arranged, the body being formed of a heat conductive material; and
   means for thermostatically controlling the temperature of said body.

6. The liquid analyzing apparatus according to claim 5 and further comprising a diluent reservoir and means for connecting the reservoir to said mixing means, the connecting means extending around the body and being in heat conductive contact therewith.

7. An apparatus for analyzing samples of milk or related liquids mixed with diluent, said apparatus comprising:
   a homogenizer comprising a piston pump including a cylinder, a piston rod, a piston rigidly connected to one end of said piston rod, and an O-ring arranged circumferentially on said piston and sealingly engaging with the inner walls of the cylinder;
   driving means connected to the other end of said piston rod by means of a joint of the type allowing movement in all directions, and adapted to reciprocate said piston and piston rod axially while angularly oscillating them in relation to the longitudinal axis of the cylinder;
   said piston pump further including an outlet, a ball valve including a ball biased towards a valve seat by a spring member being arranged in said outlet, and a piston, displaceably and sealingly arranged in a cylindrical bore, being interposed between and engaging said ball and said biasing spring member.

8. An apparatus according to claim 7, further comprising a backing ring of plastic material for supporting said O-ring.

9. An apparatus according to claim 8, wherein said backing ring is made of tetrafluorpolyethylene.

10. An apparatus according to claim 7, wherein said driving means comprise a manually operable driving handle.

11. An apparatus according to claim 7, wherein said cylinder of the piston pump is positioned in a body made from a heat conductive material and provided with a thermostatically controlled heating device.

12. An apparatus according to claim 11, wherein said body is surrounded by a heat insulating layer.

13. An apparatus according to claim 12, further comprising a diluent reservoir and mixing means for mixing a liquid sample with diluent, the diluent reservoir being connected to said mixing means by a passage extending around said body and being in heat conductive contact therewith.

14. An apparatus according to claim 11, further comprising a photometric measuring device positioned within said body and communicating with the outlet of the homogenizer for measuring a constituent of a sample contained in said mixture.

15. An apparatus according to claim 14, wherein said photometric measuring device comprises a cuvette communicating with the outlet of the homogenizer, a valve adapted to secure a superatmospheric pressure within the cuvette being arranged downstream of the cuvette.

16. A liquid analyzing apparatus for determining the fat content of milk samples or the like, comprising means for mixing a liquid sample with diluent and means for homogenizing the mixture of the liquid sample and diluent and for passing the homogenized mixture to photometric measuring means adapted to measure a constituent of the sample in the mixture, the homogenizing means and the photometric measuring means being arranged within a body which is made from a heat conductive material and which has means for thermostatically controlling the temperature of said body and a spillage collection tray, the photometric measuring means having a discharge conduit connected to a passage for discharge of liquid from said tray, so that liquid discharged from said homogenizing means creates suction in said discharge passage.

17. An apparatus for analyzing samples of milk or related liquids mixed with diluent, said apparatus comprising,
(a) a homogenizer comprising a piston pump having a cylinder, a piston rod, a piston rigidly connected to one end of said piston rod, and an O-ring arranged circumferentially on said piston and sealingly engaging with the inner walls of the cylinder;
(b) driving means connected to the other end of said piston rod, said connection being by means of a joint which allows movement in all directions and adapted to reciprocate said piston and piston rod axially while angularly oscillating them in relation to the longitudinal axis of the cylinder; and
(c) a spillage collecting tray, the outlet of the homogenizer being connected to a passage for discharge of liquids from said tray so that liquid discharged from the homogenizer creates a suction in said discharge passage.

* * * * *